US012642505B2

(12) United States Patent
Kumata

(10) Patent No.: US 12,642,505 B2
(45) Date of Patent: Jun. 2, 2026

(54) ULTRASOUND TRANSDUCER ARRAY, ENDOSCOPE, AND MANUFACTURING METHOD OF ULTRASOUND TRANSDUCER ARRAY

(71) Applicant: OLYMPUS CORPORATION, Tokyo (JP)

(72) Inventor: Yuya Kumata, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 384 days.

(21) Appl. No.: 18/218,779

(22) Filed: Jul. 6, 2023

(65) Prior Publication Data

US 2023/0346348 A1      Nov. 2, 2023

Related U.S. Application Data

(63) Continuation of application No. PCT/JP2021/014028, filed on Mar. 31, 2021.

(51) Int. Cl.
A61B 8/00 (2006.01)
A61B 1/00 (2006.01)
H01L 23/498 (2006.01)

(52) U.S. Cl.
CPC ........ A61B 8/4488 (2013.01); A61B 1/00018 (2013.01); H01L 23/4985 (2013.01); A61B 1/00009 (2013.01)

(58) Field of Classification Search
CPC ..... A61B 1/0009; A61B 1/00018; A61B 1/04; A61B 1/05; A61B 1/0625; A61B 8/12;

(Continued)

(56) References Cited

U.S. PATENT DOCUMENTS

| | | | |
|---|---|---|---|
| 2015/0279764 A1 | 10/2015 | Yamada | |
| 2019/0231313 A1* | 8/2019 | Saroha | ................. A61B 8/4488 |
| 2020/0205777 A1* | 7/2020 | Kumata | ................... A61B 8/12 |

FOREIGN PATENT DOCUMENTS

| | | | |
|---|---|---|---|
| JP | H01-291846 A | 11/1989 | |
| JP | H01-291847 A | 11/1989 | |

(Continued)

OTHER PUBLICATIONS

International Search Report dated Jun. 8, 2021 received in PCT/JP2021/014028.

*Primary Examiner* — Boniface N Nganga
(74) *Attorney, Agent, or Firm* — Scully, Scott, Murphy & Pressser, P.C.

(57) ABSTRACT

An ultrasound transducer array includes: a transducer group including a plurality of ultrasound transducers aligned, the transducers being configured to transmit and receive ultrasonic waves; a signal line configured to electrically connect the transducer group and an external device and transmit a signal communicated by the transducer group and the external device; and a relay board that is a bendable relay board and that has a first end and a second end, the first end being branched, the first end being connected to each of the ultrasound transducers, the second end being connected to the signal line to relay transmission and reception of the signal between the ultrasound transducers and the signal line, branched portions of the first end of the relay board extending in a direction of alignment of the ultrasound transducers.

9 Claims, 9 Drawing Sheets

(58) Field of Classification Search
CPC ... A61B 8/4483; A61B 8/4488; A61B 8/4494;
H01L 23/4985
See application file for complete search history.

(56)                    References Cited

FOREIGN PATENT DOCUMENTS

| WO | 2014/091970 A1 | 6/2014 |
| WO | 2017/169374 A1 | 10/2017 |

* cited by examiner

ULTRASOUND TRANSDUCER ARRAY, ENDOSCOPE, AND MANUFACTURING METHOD OF ULTRASOUND TRANSDUCER ARRAY

CROSS-REFERENCE TO RELATED APPLICATION

This application is a continuation of International Application No. PCT/JP2021/014028, filed on Mar. 31, 2021, the entire contents of which are incorporated herein by reference.

BACKGROUND

1. Technical Field

The present disclosure relates to an ultrasound transducer array, and a manufacturing method of an endoscope and an ultrasound transducer array.

2. Related Art

In the related, in the medical field, an endoscope system has been used when an organ of a subject, such as a patient, is observed. The endoscope system includes an endoscope in which, for example, an imaging device, an ultrasound device, and the like are arranged at a distal end, and that includes an insertion portion to be inserted into the inside of a subject, and a processing device that is connected to a proximal end side of the insertion portion through a cable, and that subjects a signal generated by the device to image processing, to display an image on a display and the like.

The ultrasound device includes plural ultrasound transducers. The respective ultrasound transducers are electrically connected to the processing device through an ultrasonic cable at a distal end portion of the endoscope (for example, WO2017/169374). In WO2017/169374, respective ultrasound transducers and a signal line of an ultrasonic cable are electrically connected through a flexible substrate.

SUMMARY

In some embodiments, an ultrasound transducer array includes: a transducer group including a plurality of ultrasound transducers aligned, the transducers being configured to transmit and receive ultrasonic waves; a signal line configured to electrically connect the transducer group and an external device and transmit a signal communicated by the transducer group and the external device; and a relay board that is a bendable relay board and that has a first end and a second end, the first end being branched, the first end being connected to each of the ultrasound transducers, the second end being connected to the signal line to relay transmission and reception of the signal between the ultrasound transducers and the signal line, branched portions of the first end of the relay board extending in a direction of alignment of the ultrasound transducers.

In some embodiments, an endoscope includes: an insertion portion configured to be inserted to an inside of a subject; and an ultrasound transducer array that includes a transducer group that is arranged at a distal end of the insertion portion and that includes a plurality of ultrasound transducers aligned, the transducers being configured to transmit and receive ultrasonic waves; a signal line configured to electrically connect the transducer group and an external device and transmit a signal communicated by the transducer group and the external device; and a relay board that is a bendable relay board and that has a first end and a second end, the first one end being branched, the first end being connected to each of the ultrasound transducers, the second end being connected to the signal line to relay transmission and reception of the signal between the ultrasound transducers and the signal line, branched portions of the first end of the relay board extending in a direction of alignment of the ultrasound transducers.

In some embodiments, provided is a manufacturing method of an ultrasound transducer array. The method includes: arranging branched portions of a bendable relay board, one end of which is branched, in a direction of alignment of a plurality of ultrasound transducers configured to transmit and receive ultrasonic waves, with respect to the ultrasound transducers; and electrically connecting the ultrasound transducers and the relay board.

In some embodiments, an ultrasound transducer array includes: a transducer group including a plurality of ultrasound transducers aligned, the transducers being configured to transmit and receive ultrasonic waves; a signal line configured to electrically connect the transducer group and an external device and transmit a signal communicated by the transducer group and the external device; and a relay board having a first end and a second end, the first end being connected to each of the ultrasound transducers, the second end being connected to the signal line to relay transmission and reception of the signal between the ultrasound transducers and the signal line, the relay board including an opening portion configured to expose a part of the ultrasound transducers, the relay board being electrically connected to the ultrasound transducers at a portion extending in a direction of alignment of the ultrasound transducers in peripheral portions of the opening portion.

The above and other features, advantages and technical and industrial significance of this disclosure will be better understood by reading the following detailed description of presently preferred embodiments of the disclosure, when considered in connection with the accompanying drawings.

DETAILED DESCRIPTION

Hereinafter, forms to implement the disclosure (hereinafter, embodiments) will be explained with reference to the drawings. The embodiments explained below are not intended to limit the disclosure. Furthermore, in descriptions of the drawings, the same reference symbols are assigned to the same components.

First Embodiment

Figure 1:
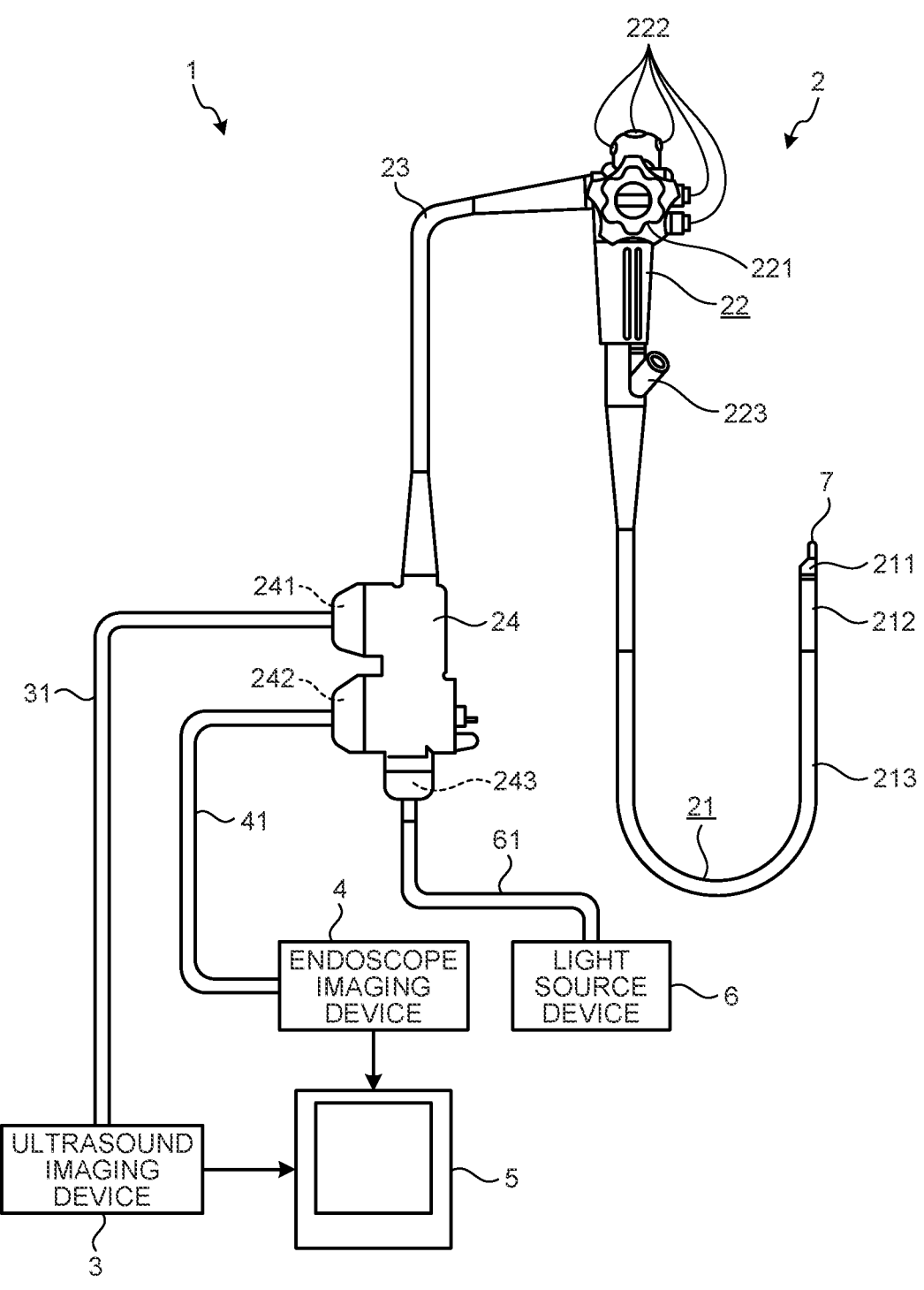
FIG. 1 is a diagram schematically illustrating an endoscope system according to a first embodiment of the disclosure.

FIG. 1 is a diagram schematically illustrating an endoscope system 1 according to a first embodiment of the disclosure. The endoscope system 1 is a system to perform ultrasound diagnosis of the inside of a subject, such as human, by using an ultrasound endoscope. This endoscope system 1 includes an ultrasound endoscope 2, an ultrasound imaging device 3, an endoscope imaging device 4, a display device 5, and a light source device 6.

The ultrasound endoscope 2 includes an imaging optical system and an imaging device, is inserted into a digestive tract (esophagus, stomach, duodenum, large intestine) or a respiratory organ (trachea, bronchus) of a subject, and is capable of capturing an image of either of the digestive tract or the respiratory organ. The ultrasound endoscope 2 includes a light guide that guides illumination light to be irradiated to the subject at the time of imaging. This light guide is provided with light that is guided by an optical fiber cable 61 described later, and its distal end reaches a distal end of an insertion portion of the ultrasound endoscope 2 to be inserted into the subject, while its proximal end is connected to the light source device 6 that generates the illumination light. Moreover, the ultrasound endoscope 2 transmits ultrasonic waves to a digestive tract or peripheral organs (pancreas, gallbladder, bile duct, biliary tract, lymph node, mediastinal organ, blood vessel, etc.) of the respiratory organ, and receives ultrasonic waves reflected on the peripheral organs.

The ultrasound endoscope 2 includes an insertion portion 21, an operating portion 22, an universal cord 23, and a connector 24. The insertion portion 21 is a portion that is inserted in the subject. This insertion portion 21 is arranged on a distal end side of the ultrasound endoscope 2, and includes a rigid distal end portion 211 including a transducer portion 7, a bendable portion 212 that is connected to a proximal end side of the distal end portion 211 and is bendable, and a flexible tube portion 213 that is connected to a proximal end side of the bendable portion 212, and has flexibility. Inside the insertion portion 21, although specific illustration is omitted, a light guide to transmit illumination light supplied by the light source device 6 and plural signal lines including a signal line (signal line 81) described later to transmit various kinds of signals are drawn through, and a treatment-tool insertion path to insert through a treatment tool, and the like are formed.

The transducer portion 7 is constituted of plural ultrasound transducers (transducer group) arranged in an array. The ultrasound transducer is constituted using a piezoelectric element. The transducer portion 7 composes a convex ultrasound transducer array that performs electronic scanning by electronically switching devices to be involved in transmission and reception, or by delaying transmission and reception of the respective devices. The transducer portion 7 irradiates ultrasonic waves to a subject to be observed as the ultrasound transducers vibrate upon input of a pulse signal. Moreover, ultrasonic waves returned from the subject to be observed propagate to the respective ultrasound transducers. The ultrasound transducers are vibrated by the ultrasonic waves, and converts the vibration into an electrical echo signal, to output to the ultrasound imaging device 3.

The operating portion 22 is a portion that is connected to the proximal end side of the insertion portion 21, and that accepts various kinds of operations from a user, such as doctor. This operating portion 22 includes a bending knob 221 to perform a bending operation of the bendable portion 212, and plural operating members 222 to perform various kinds of operations. Furthermore, in the operating portion 22, a treatment tool inlet 223 that communicates with the treatment-tool insertion path, and that is to insert a treatment tool into the treatment-tool insertion path is formed.

The universal cord 23 extends from the operating portion 22, and is a cable in which plural signal cables to transmit various kinds of signals, an optical fiber to transmit illumination light supplied from the light source device 6, and the like are arranged.

The connector 24 is arranged at a distal end of the universal cord 23. The connector 24 includes a first to a third connector portions 241 to 243 to which an external ultrasonic-signal cable 31, a video cable 41, and the optical fiber cable 61 are connected, respectively.

The ultrasound imaging device 3 is electrically connected to the ultrasound endoscope 2 through the external ultrasonic-signal cable 31, and outputs a pulse signal to the ultrasound endoscope 2 through the external ultrasonic-signal cable 31 and receives an input of an echo signal from the ultrasound endoscope 2. The ultrasound imaging device 3 generates ultrasonic image data by performing predetermined processing on the echo signal.

The endoscope imaging device 4 is electrically connected to the ultrasound endoscope 2 through the video cable 41, and receives an input of an image signal from the ultrasound endoscope 2 through the video cable 41. The endoscope imaging device 4 generates endoscopic image data by performing predetermined processing on the image signal.

The display device 5 is constituted of a liquid crystal or an organic electroluminescence (EL) display, a projector, a cathode ray tube (CRT) display, and the like, and displays an ultrasound image generated by the ultrasound imaging device 3, an endoscope image generated by the endoscope imaging device 4, and the like.

The light source device 6 is connected to the ultrasound endoscope 2 through the optical fiber cable 61, and supplies illumination light to illuminate the inside of a subject to the ultrasound endoscope 2 through the optical fiber cable 61.

Figure 2:
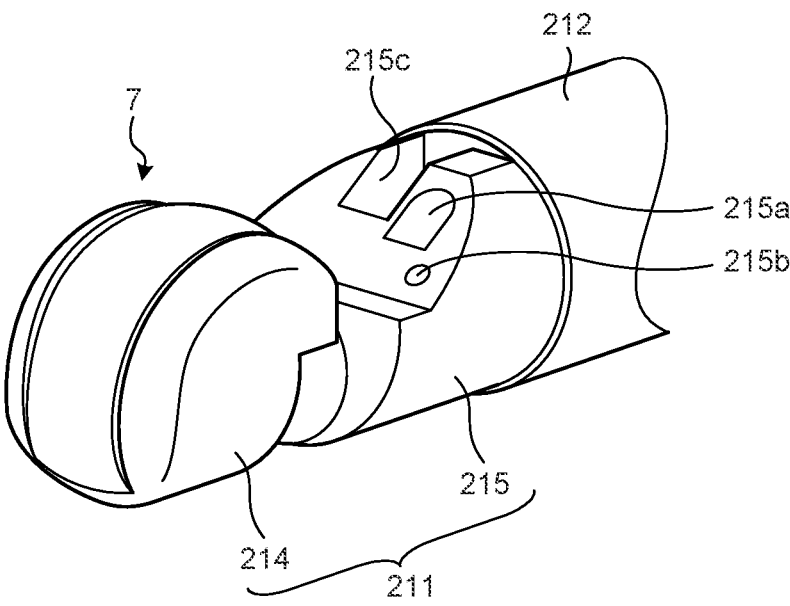
FIG. 2 is a perspective view illustrating a distal end configuration of an insertion portion of an ultrasound endoscope according to the first embodiment of the disclosure.

FIG. 2 is a perspective view schematically illustrating a distal end configuration of the insertion portion 21 of the ultrasound endoscope 2 according to the first embodiment. The distal end portion 211 includes an ultrasound transducer module 214 that holds the transducer portion 7, and an endoscope module 215 that forms a part of the imaging optical system and has an objective lens 215a that takes in light from the outside, an imaging device, and an illumination lens 215b that gathers illumination light to emit to the outside. In the endoscope module 215, a treatment-tool protruding outlet 215c that communicates with the treatment-tool insertion path formed in the insertion portion 21, and through which a treatment tool is projected from the distal end of the insertion portion 21 is formed. The treatment-tool insertion path is arranged such that a portion near an end portion continuous to the treatment-tool protruding output 215c is slanted with respect to a longitudinal axis of the insertion portion 21, and a treatment tool protrudes in a direction slanted with respect to the longitudinal axis from the treatment-tool protruding outlet 215c. The longitudinal axis herein is an axis along a longitudinal direction of the insertion portion 21. In the bendable portion 212 and the flexible tube portion 213, the axial direction changes depending on respective positions, but in the rigid distal end portion 211, the longitudinal axis is stable straight axis.

Figure 3:
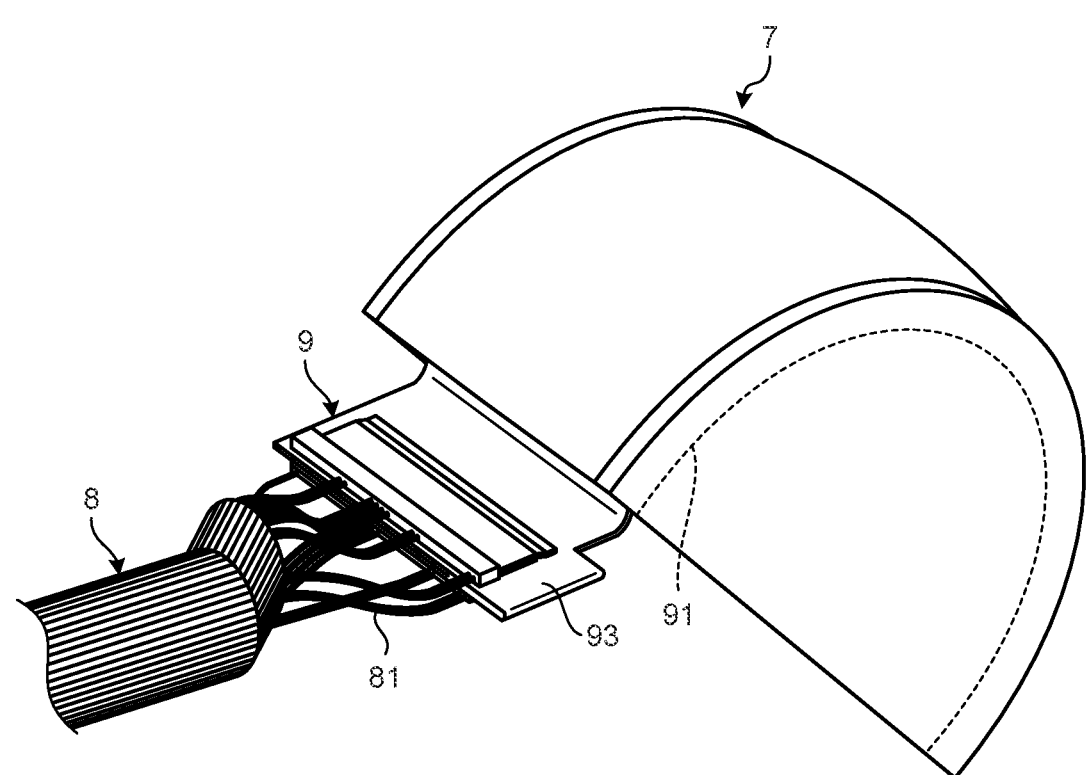
FIG. 3 is a perspective view schematically illustrating a configuration of an ultrasound transducer array included in the ultrasound endoscope according to the first embodiment of the disclosure.
Figure 4:
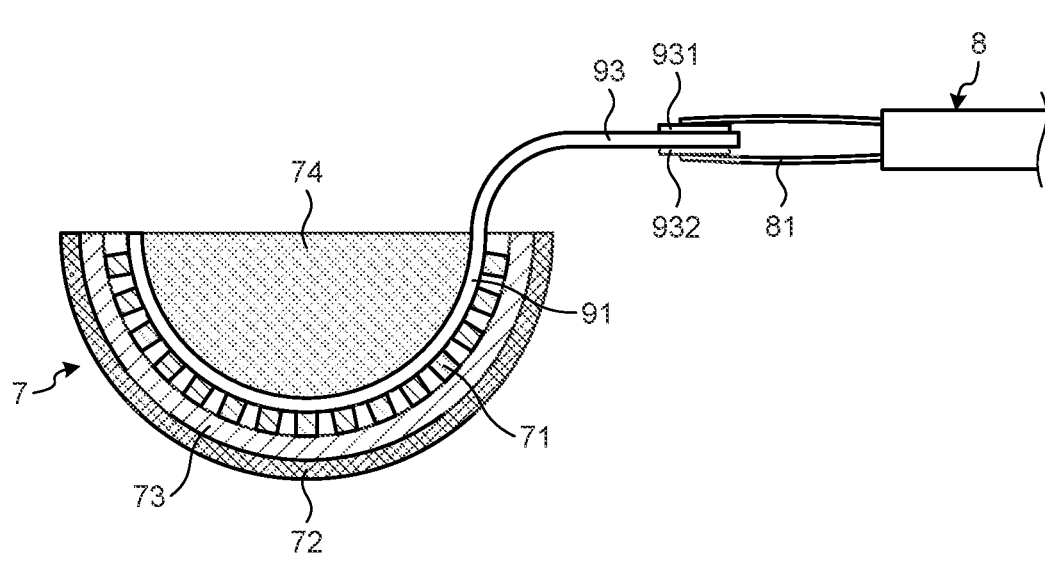
FIG. 4 is a cross-section illustrating a configuration of the ultrasound transducer array included in the ultrasound endoscope according to the first embodiment of the disclosure.
Figure 5:
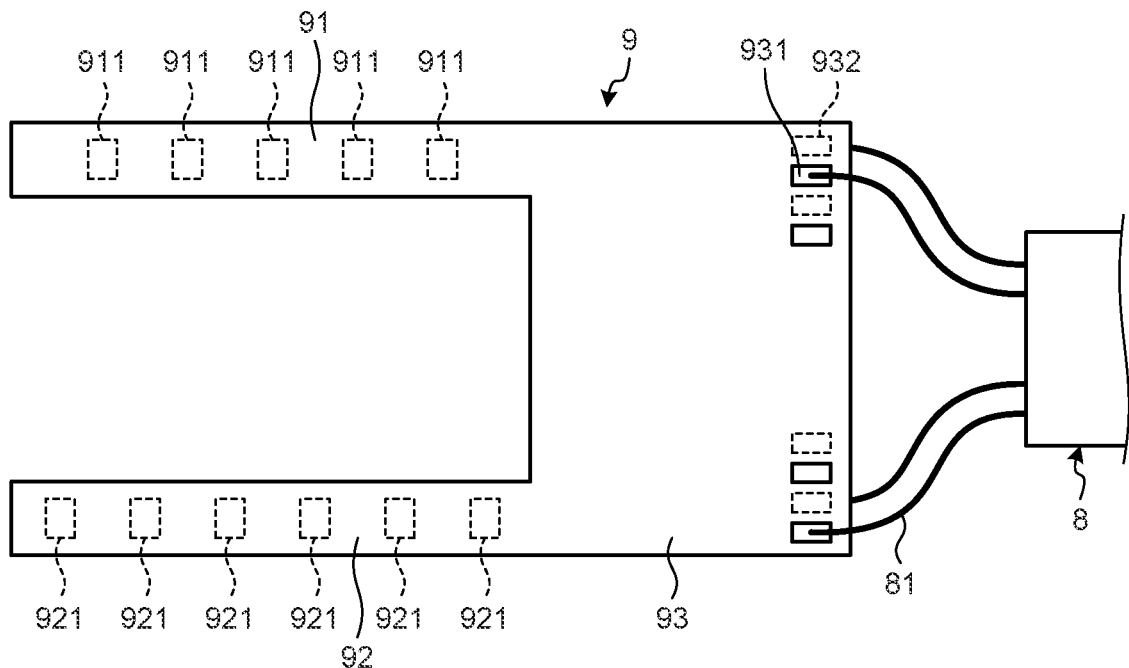
FIG. 5 is a plan view illustrating a configuration of a relay board of the ultrasound transducer array included in the ultrasound endoscope according to the first embodiment of the disclosure.

Subsequently, a configuration of the transducer portion 7 at the distal end portion 211 of the insertion portion 21 will be explained, referring to FIG. 3 to FIG. 5. FIG. 3 is a perspective view schematically illustrating a configuration of the ultrasound transducer array included in the ultrasound endoscope according to the first embodiment of the disclosure. FIG. 4 is a cross-section illustrating a configuration of the ultrasound transducer array included in the ultrasound endoscope according to the first embodiment of the disclosure. FIG. 5 is a plan view illustrating a configuration of a relay board of the ultrasound transducer array included in the ultrasound endoscope according to the first embodiment of the disclosure.

The ultrasound transducer module 214 is constituted of the transducer portion 7 and a relay board 9 that forms a part of a path to electrically connect the transducer portion 7 and the ultrasound imaging device 3, and that relays electrical connection between the transducer portion 7 and an internal ultrasonic-signal cable 8, housed in a casing. The transducer portion 7, the internal ultrasonic-signal cable 8, and the relay board 9 constitute the ultrasound transducer array. It may be configured to use a long bendable flexible printed circuit (FPC) instead of the internal ultrasonic-signal cable 8.

The transducer portion 7 is connected to the internal ultrasonic-signal cable 8 through the relay board 9. The internal ultrasonic-signal cable 8 is electrically connected to the external ultrasonic-signal cable 31. The internal ultrasonic-signal cable 8 includes plural signal lines 81. The respective signal lines 81 are electrically connected to the corresponding ultrasound transducers 71 through the relay board 9. FIG. 3 illustrates a simplified structure to facilitate explanation, but coaxial wires are provided according to the number of piezoelectric devices in an actual situation.

The transducer portion 7 includes the ultrasound transducers 71 (hereinafter, it may be denoted simply as transducers 71) that each form a prism shape, and are arranged such longitudinal directions of the transducers 71 are aligned, an acoustic lens 72 that forms an outer surface of the transducer portion 7, an acoustic matching layer 73 that is arranged between the transducers 71 and the acoustic lens 72, and a backing material 74 that is arranged on a side opposite to a side of the acoustic matching layer 73 with respect to the transducers 71 (refer to FIG. 4). The respective transducers 71 are electrically connected to the relay board 9.

The relay board 9 is branched into two at an end portion on one end side of the relay board 9, and is connected to the transducer 71 on the branched side and is connected to the internal ultrasonic-signal cable 8 at an end portion on another end side of the relay board 9. The relay board 9 includes a first extension portion 91, a second extension portion 92, and a connection portion 93 (refer to FIG. 5). The relay board 9 is constituted of an FPC. The relay board 9 is formed by arranging wiring patterns on a substrate made by using polyimide. The substrate constituting the relay board 9 is constructed, for example, by laminating plural substrates. On the respective layers, predetermined wiring patterns are formed, respectively. Moreover, on a surface of an outermost layer of the substrate, for example, a coverlay is arranged. Hereinafter, a surface having the largest area is referred to as "main surface".

The first extension portion 91 is arranged on one end side of a longitudinal direction of the transducer 71, extends in a direction of alignment of the transducers 71, and is connected to some of the transducers 71. In the first extension portion 91, plural electrode portions 911 (first electrode portions) connected to the transducers 71, respectively, are formed.

The second extension portion 92 is arranged on another end side of the longitudinal direction of the transducer 71, extends in the direction alignment of the transducers 71, and is connected to the transducers 71 different from the transducers connected to the first extension portion 91. In the second extension portion 92, plural electrode portions 921 (second electrode portions) that are connected to the transducers 71, respectively, are formed. The respective electrode portions 911 and 921 are connected to the transducers 71 different from each other.

The connection portion 93 has one end that is connected to the first extension portion 91 and the second extension portion 92, and another end that is connected to the internal ultrasonic-signal cable 8. In the connection portion 93, plural electrode portions 931 and 932 (third electrode portions) that are respectively connected to the signal lines 81 are formed. The electrode portions 931 and 932 are exposed on the main surfaces that are different surfaces from each other, and that form a pair opposing each other in the relay board 9. In FIG. 5, the electrode portion 931 is exposed on a surface opposite to a surface on which the electrode portions 911 and 921 are exposed, and the electrode portion 932 is exposed on a surface on the same side as the surface on which the electrode portions 911 and 921 are exposed.

In the relay board 9, the first extension portion 91 is connected to an end portion of the connection portion 93 on the opposite side to the side on which the electrode portions 931 and 932 are formed and on one end side of a direction of alignment of the electrode portion 931 (or 932) of the connection portion 93. Moreover, the second extension portion 92 is connected to an end portion of the connection portion 93 on the opposite side to the side on which the electrode portions 931 and 932 are formed and on another end of the direction of alignment of the electrode portion 931 (or 932). The first extension portion 91 and the second extension portion 92 are preferable to be arranged at a position outside a region in which the transducers 71 transmits and receives ultrasonic waves (effective region). The relay board 9 illustrated in FIG. 5 shows an example in which the main surface is in a C-shape, but the arrangement of the first extension portion 91 and the second extension portion 92 (connection positions to the connection portion 93) is not limited thereto.

Figure 6:
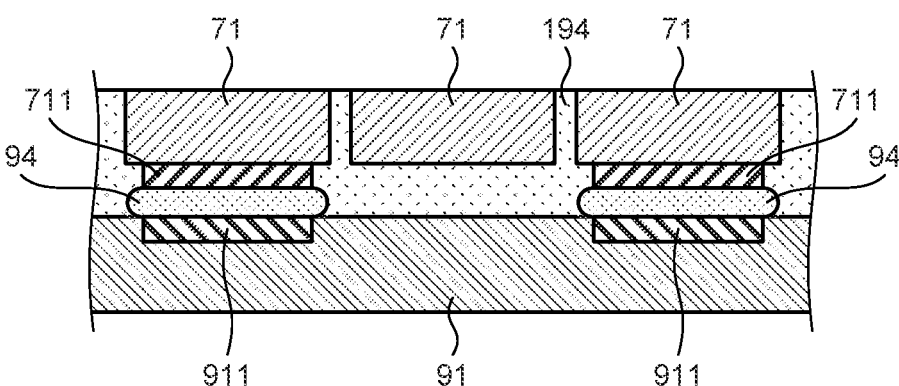
FIG. 6 is a diagram (Part 1) for explaining a manufacturing method of the ultrasound transducer array included in the ultrasound endoscope according to the first embodiment of the disclosure.
Figure 7:
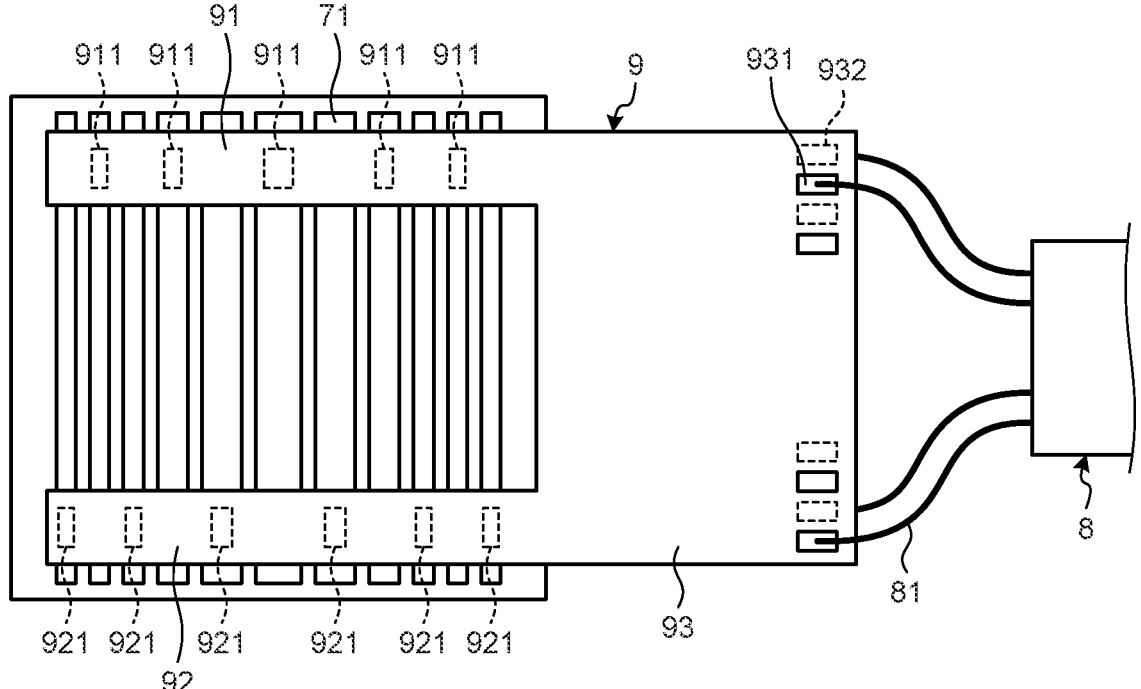
FIG. 7 is a diagram (Part 2) for explaining the manufacturing method of the ultrasound transducer array included in the ultrasound endoscope according to the first embodiment of the disclosure.
Figure 8:
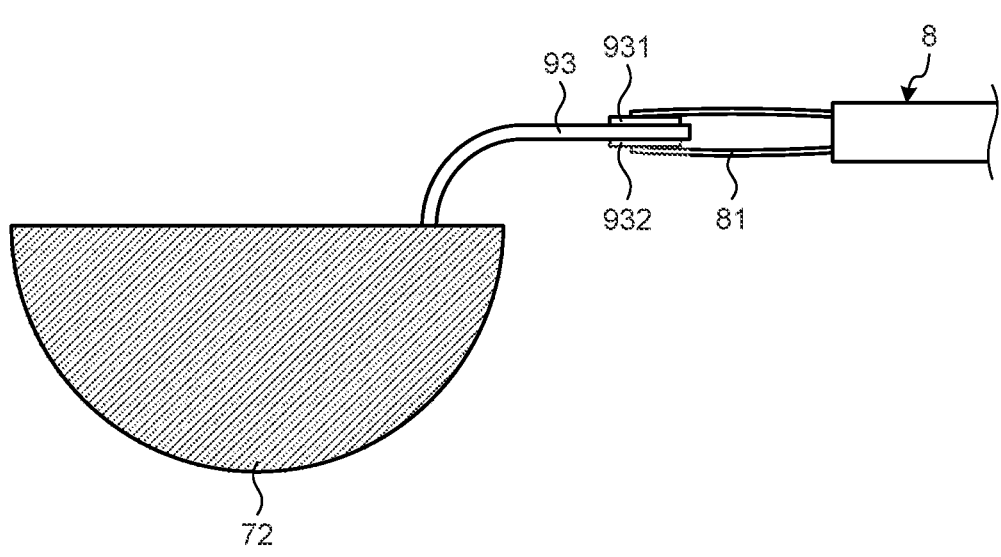
FIG. 8 is a diagram (Part 3) for explaining the manufacturing method of the ultrasound transducer array included in the ultrasound endoscope according to the first embodiment of the disclosure.

Next, a manufacturing method of the ultrasound transducer array at the time of manufacturing the ultrasound endoscope 2 will be explained, referring to FIG. 5 to FIG. 8. FIG. 6 to FIG. 8 are diagrams for explaining the manufacturing method of the ultrasound transducer array included in the ultrasound endoscope according to the first embodiment of the disclosure. FIG. 6 is a cross-section illustrating a connecting portion between the transducer 71 and the first extension portion 91, and is a cross-section cut along a plane perpendicular to the longitudinal direction of the transducer 71. In FIG. 6 to FIG. 8 in the following, a part of the signal line 81, the electrodes on the board, and the like are omitted.

First, the signal lines 81 are connected to the electrode portions 931 and 932 of the relay board 9 (refer to FIG. 5). The electrode portions 931 and 932 are arranged alternately in a plan view from a direction perpendicular to the main surface of the relay board 9. This arrangement can increase a gap between the electrode portions 931 adjacent to each other, and a gap between the electrodes 932 adjacent to each other.

After the signal lines 81 are connected to the relay board 9, the corresponding electrode portions 911 and 921 are arranged with respect to the respective aligned transducers 71. At this time, the electrode portions 911 are not connected to all the transducers 71 adjacent to each other in the direction of alignment. Moreover, the electrode portions 921 are not connected to all the transducers 71 adjacent to each other in the direction of alignment either. That is, the aligned transducers 71 are connected to the electrode portions 911 and 921 alternately.

After the electrode portions 911 and 921 are arranged on the transducers 71, electrodes 711 formed on the transducers 71 are connected to the electrode portions 911 and 921 (refer to FIG. 6). On the electrode portions 911 and 921, or on the electrode 711, an adhesive 94 is applied in advance, and the adhesive 94 bonds the electrode portions 911, 921 and the electrodes 711 by thermal compression bonding. The adhesive 94 is made using a material having electrical conductivity, and is cured by heat. Examples of the adhesive 94 include an anisotropic conductive paste (ACP). In an entire space formed between the respective transducers 71 and the relay board 9, an adhesive 194 having no electrical conductivity is filled.

As an actual manufacturing sequence, the transducers 71 are laminated on the acoustic matching layer 73 that is formed in an arc shape in advance, and subsequently, the electrodes 711 formed in the transducers 71 are connected to the electrode portions 911 and 921 of the relay board 9. Thereafter, the backing material 74 (refer to FIG. 4) formed as a block having a portion formed in an arc shape in advance and the relay board 9 (on which the respective transducers 71 are mounted) are bonded.

A method of arranging the acoustic matching layer 73 after the transducers 71 are mounted on the relay board 9 (by arranging the transducers 71 connected to the relay board 9 on the acoustic matching layer 73 that is formed in an arc shape in advance, the transducer group is aligned in an arc shape: refer to FIG. 7), and then arranging the backing material 74, or a method of arranging the acoustic matching layer 73 on the transducers 71 before the electrode portions 911 and 921 are connected to the transducers 71 may be adopted.

After the acoustic matching layer 73 and the backing material 74 are arranged, the acoustic matching layer 73 and the backing material 74 are covered with the acoustic lens 72 (refer to FIG. 8). By the processing explained above, the ultrasound transducer array illustrated in FIG. 3 is manufactured.

Connection of the relay board 9 and the signal lines 81 is not limited to be performed before connection of the relay board 9 and the transducers 71, but it may be performed after connection of the relay board 9 and the transducers 71, or may be performed after arrangement of the acoustic matching layer 73 and the backing material 74.

In the first embodiment explained above, the relay board 9 that relays signal transmission between the transducer 71 and the signal line 81 has a bifurcated structure at an end portion of the relay board 9 on a side connected to the transducers 71, and the electrode portions 911 and 921 formed in the first extension portion 91 and the second extension portion 92 constituting the bifurcated structure are connected to the respective transducers 71. By splitting connection to the transducers 71 into two, a distance between electrodes can be increased. By increasing the distance between the electrodes, when bending the relay board 9 on which the transducers 71 are mounted to form the relay board 9 into an arc shape, deviation in movement between the respective transducers 71 and the electrode portions (electrode portions 911, 921) arranged on the relay board 9 can be absorbed respectively by branched bifurcated portions. As a result, misalignment of connection positions of the electrode portions 911 and 921 with respect to the respective transducers 71 are suppressed. According to the first embodiment, by suppressing misalignment of connection positions of the electrode portions 911 and 921 with respect to the transducers 71, it is possible to prevent possibilities of occurrence of wire breakage, a short circuit, and the like originated from the misalignment of correction positions more reliably, leading to, as a result, suppression of possibilities of deterioration of quality of ultrasound transducers.

Furthermore, according to the first embodiment, with a configuration in which the first extension portion 91 and the second extension portion 92 are connected alternately to the aligned transducers 71 and, therefore, an interval between the transducers 71 can be decreased while maintaining a distance between the electrode portions. Moreover, if a distance between the electrode portions of the respective extension portions can be maintained large, it is possible to suppress noises originated from the signal line 81, or suppress a short circuit.

Moreover, according to the first embodiment, by splitting the relay board 9 into two, the backing material 74 is filled in a gap between the transducers 71, and unnecessary reflection of ultrasonic waves can be suppressed.

Second Embodiment

Figure 9:
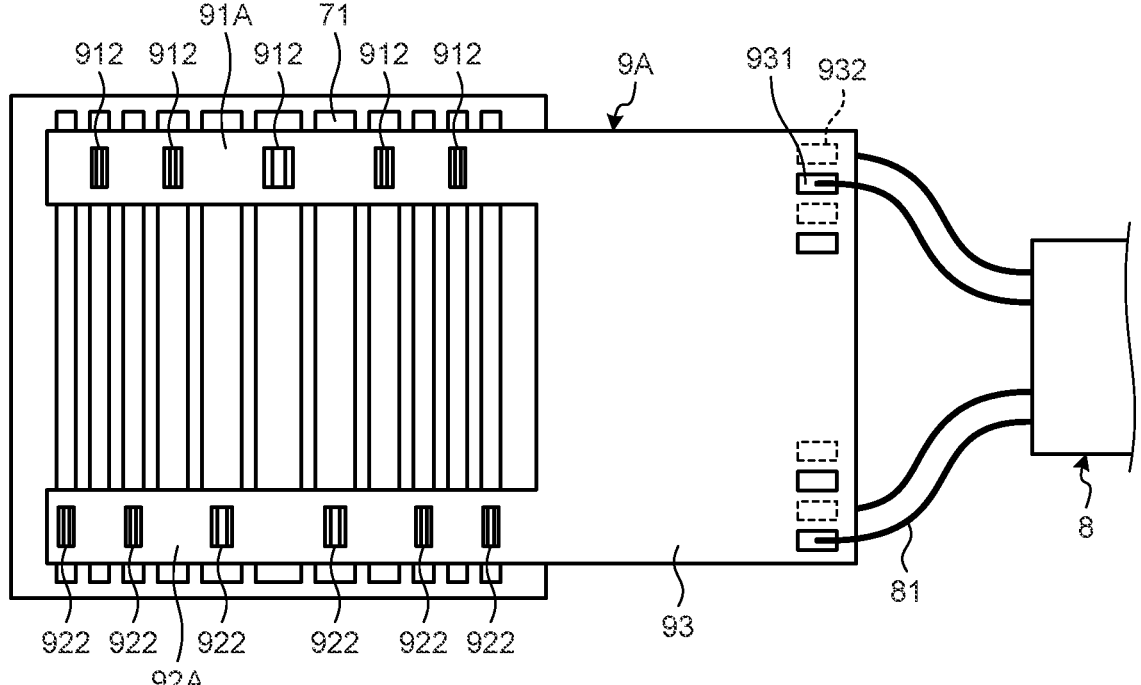
FIG. 9 is a diagram (Part 1) illustrating a configuration of an essential part of an ultrasound transducer array included in an ultrasound endoscope according to a second embodiment of the disclosure.
Figure 10:
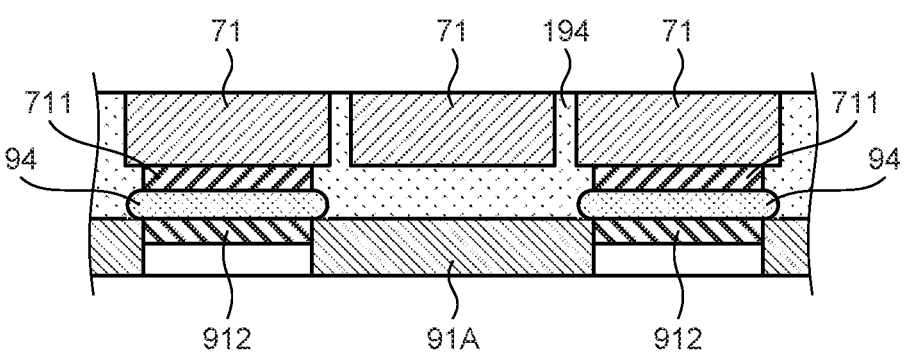
FIG. 10 is a diagram (Part 2) illustrating a configuration of the essential part of the ultrasound transducer array included in the ultrasound endoscope according to the second embodiment of the disclosure.

Next, a second embodiment of the disclosure will be explained, referring to FIG. 9 and FIG. 10. FIG. 9 and FIG. 10 are diagrams illustrating a configuration of an essential part of the ultrasound transducer array included in the ultrasound endoscope according to the second embodiment of the disclosure. FIG. 10 is a cross-section illustrating a connection portion of the transducer 71 and a first extension portion 91A, and is a cross-section cut along a plane perpendicular to the longitudinal direction of the transducer 71. An endoscope system according to the second embodiment has a configuration similar to the endoscope 1 described above except a change in the relay board. In the second embodiment, instead of the relay board 9 of the first embodiment described above, a relay board 9A is provided. In the following, a configuration different from the first embodiment described above (relay board 9A) will be explained.

The relay board 9A is branched at an end portion on one end side of the relay board 9A, and is connected to the transducer 71 on the branched side and is connected to the internal ultrasonic-signal cable 8 at an end portion on another end side of the relay board 9A. The relay board 9A includes the first extension portion 91A, a second extension portion 92A, and the connection portion 93 (refer to FIG. 9). The relay board 9A is constituted of a bendable FPC similarly to the relay board 9 described above.

The first extension portion 91A is arranged on one end side of the longitudinal direction of the transducer 71, extends in the direction of alignment of the transducers 71, and is connected to some of the transducers 71. In the first extension portion 91A, plural electrode portions 912 respectively connected to the transducers 71 are formed.

The second extension portion 92A is arranged on another end side of the longitudinal direction of the transducer 71, extends in the direction of alignment of the transducers 71, and is connected to the transducers 71 different from the transducers 71 connected to the first extension portion 91A. In the second extension portion 92A, plural electrode portions 922 respectively connected to the transducers 71, are formed.

The connection portion 93 has one end that is connected to the first extension portion 91A and the second extension portion 92A end, and another end that is connected to the internal ultrasonic-signal cable 8. The connection portion 93 has a configuration similar to the first embodiment.

In the relay board 9A, the first extension portion 91A is connected to an end portion of the connection portion 93 on the opposite side to the side on which the electrode portions 931 and 932 are formed and on one end side of the direction of alignment of the electrode portion 931 (or 932) of the connection portion 93. Moreover, the second extension portion 92A is connected to an end portion of the connection portion 93 on the opposite side to the side on which the electrode portions 931 and 932 are formed and on another end of the direction of alignment of the electrode portion 931 (or 932). The relay board 9A illustrated in FIG. 9 shows an example in which the main surface is in a C-shape, but the arrangement of the first extension portion 91A and the second extension portion 92A (connection positions to the connection portion 93) is not limited thereto.

The electrode portions 912 and 922 are connected to the different transducers 71 from each other. Each of the electrode portions 912 and 922 has a flying lead structure. Specifically, the electrode portion 912 is arranged traversing through a hole piercing through in a direction of thickness of the first extension portion 91A, and is exposed to the outside. The electrode portion 922 is arranged in a hole piercing through a direction of thickness of the second extension portion 92A, and is exposed to the outside.

The electrode portions 912, 922 are connected to the transducers 71 alternately with respect to the direction of alignment of the transducers 71.

When assembling the ultrasound transducer array, after arranging the electrode portions 912 and 922 on the transducers 71, the electrodes 711 formed in the transducers 71 are connected to the electrode portions 912, 922 (refer to FIG. 10). To the electrode portions 912 and 922, or the electrode 711, the adhesive 94 is applied in advance, and the adhesive 94 bonds the electrode portions 912, 922 and the electrodes 711 by thermal bonding. Moreover, in entire space between the respective transducers 71 and the relay board 9A, the adhesive 194 having no electrical conductivity is filled. Other processing is similar to that of the first embodiment.

In the second embodiment explained above, similarly to the first embodiment, the relay board 9A that relays signal transmission between the transducer 71 and the signal line 81 has a bifurcated structure at an end portion of the relay board 9A on a side connected to the transducers 71, and the electrode portions 912 and 922 formed in the first extension portion 91A and the second extension portion 92A are connected to the respective transducers 71. By splitting connection to the transducers 71 into two, a distance between electrodes can be increased, and an effect similar to that of the first embodiment can be obtained.

Furthermore, according to the second embodiment, because each of the electrode portions 912 and 922 has a flying lead structure, each of the electrode portions 912 and 922 can be displaced in a hole. Because the electrode portions 912 and 922 are displaceable, even when misalignment is caused between the transducers 71 and the electrode portions 912 and 922 by a difference between a curvature radius of a curve formed by the aligned transducers 71 and a curvature radius of the first extension portion 91A or the second extension portion 92A in a curved form, the electrode portions 912 and 922 can be displaced to compensate the misalignment.

Modification of Second Embodiment

Figure 11:
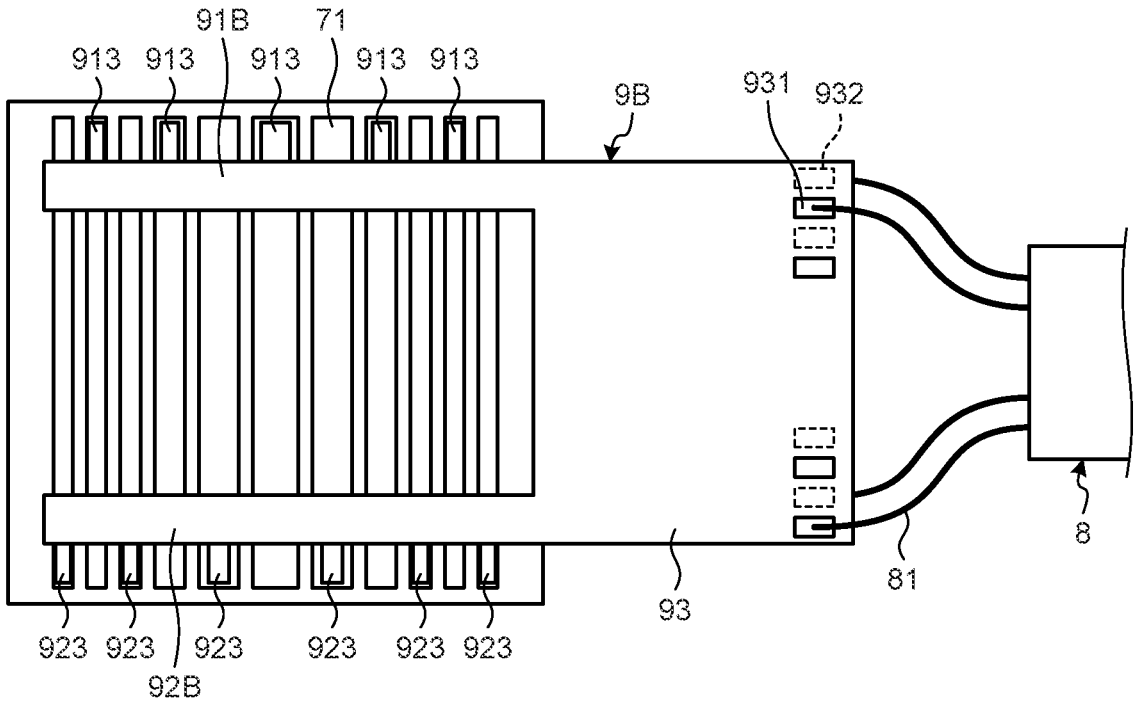
FIG. 11 is a diagram (Part 1) illustrating a configuration of an essential part of an ultrasound transducer array included in an ultrasound endoscope according to a modification of the second embodiment of the disclosure.
Figure 12:
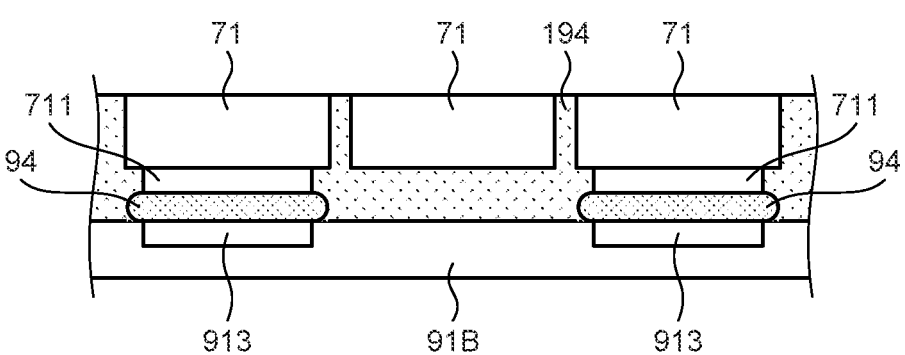
FIG. 12 is a diagram (Part 2) illustrating a configuration of the essential part of the ultrasound transducer array included in the ultrasound endoscope according to a modification of the second embodiment of the disclosure.

Next, a modification of the second embodiment of the disclosure will be explained, referring to FIG. 11 and FIG. 12. FIG. 11 and FIG. 12 are diagrams illustrating a configuration of an essential part of an ultrasound transducer array included in an ultrasound endoscope according to the modification of the second embodiment of the disclosure. FIG. 12 is a diagram illustrating a connection portion between the transducer 71 and a first extension portion 91B, and is a plan view viewed from the longitudinal direction of the transducer 71. An endoscope system according to the present modification has a configuration similar to the endoscope system 1 described above except a change in the relay board. The present modification includes a relay board 9B instead of the relay board 9 of the first embodiment described above. In the following, a configuration different from the first embodiment described above (relay board 9B) will be explained.

The relay board 9B is branched at an end portion on one end side of the relay board 9B, and is connected to the transducer 71 on the branched side and is connected to the internal ultrasonic-signal cable 8 at an end portion on another end side of the relay board 9B. The relay board 9B includes the first extension portion 91B, a second extension portion 92B, and the connection portion 93 (refer to FIG. 11). The relay board 9B is constituted of a bendable FPC similarly to the relay board 9 described above.

The first extension portion 91B is arranged one end side of the longitudinal direction of the transducer 71, extends in the direction of alignment of the transducers 71, and is connected to some of the transducers 71. In the first extension portion 91B, plural electrode portions 913 respectively connected to the transducers 71 are formed.

The second extension portion 92B is arranged on another end side of the longitudinal direction of the transducer 71, extends in the direction of alignment of the transducers 71, and is connected to the transducers 71 different from the transducers 71 connected to the first extension portion 91B. In the second extension portion 92B, plural electrode portions 923 that are respectively connected to the transducers 71 are formed.

In the relay board 9B, the first extension portion 91B is connected to an end portion of the connection portion on the opposite side to a side on which the electrode portions 931 and 932 are formed and on one end side of a direction of alignment of the electrode portion 931 (or 932) of the connection portion 93. Moreover, the second extension portion 92B is connected to an end portion of the connection portion on the opposite side to the side on which the electrode portions 931 and 932 are formed and on another end of the direction of alignment of the electrode portion 931 (or 932). The relay board 9B illustrated in FIG. 11 shows an example in which a main surface is in a C-shape, but the arrangement of the first extension portion 91B and the second extension portion 92B (connection positions to the connection portion 93) is not limited thereto.

The electrode portions 913 and 923 are connected to the different transducers 71 from each other. Each of the electrode portions 913 and 923 has a flying lead structure. Specifically, the electrode portion 913 is perpendicular to a direction in which the first extension portion 91B extends with respect to the connection portion 93, and extends from an end portion of the first extension portion 91B on the opposite side to the second extension portion B. The electrode portion 923 is perpendicular to the direction in which the first extension portion 91B extends with respect to the connection portion 93, and extends from an end portion of the first extension portion 92B on the opposite side to the second extension portion 92B.

The electrode portions 913 and 923 are connected to the transducers 71 alternately with respect to the direction of alignment of the transducers 71.

When assembling the ultrasound transducer array, after arranging the electrode portions 913 and 923 on the transducers 71, the electrodes 711 formed in the transducers 71 are connected to the electrode portions 913, 923 (refer to FIG. 12). To the electrode portions 913 and 923, or to the electrode 711, the adhesive 94 is applied in advance, and the adhesive 94 bonds the electrode portions 913, 923 and the electrodes 711 by thermal bonding. Moreover, in entire space between the respective transducers 71 and the relay board 9B, the adhesive 194 having no electrical conductivity is filled. Other processing is similar to that of the first embodiment. For the adhesive 94, other than ACP described above, solder plating may be adopted.

In the modification explained above, similarly to the first embodiment, the relay board 9B that relays signal transmission between the transducer 71 and the signal line 81 has a bifurcated structure at an end portion of the relay board 9B on a side connected to the transducers 71, and the electrode portions 913 and 923 formed in the first extension portion 91B and the second extension portion 92B are connected to the respective transducers 71. By splitting connection to the transducers 71 into two, a distance between electrodes can be increased, and an effect similar to that of the first embodiment can be obtained.

Furthermore, according to the present modification, because each of the electrode portions 913 and 923 has a flying lead structure, each of the electrode portions 913 and 923 can be displaced in a hole similarly to the second embodiment described above. Because the electrode portions 913 and 923 are displaceable, even when misalignment is caused between the transducers 71 and the electrode portions 913 and 923 by a difference between a curvature radius of a curve formed by the aligned transducers 71 and a curvature radius of the first extension portion or the second extension portion 92A in a curved form, the electrode portions 913 and 923 can be displaced to compensate the misalignment.

Third Embodiment

Figure 13:
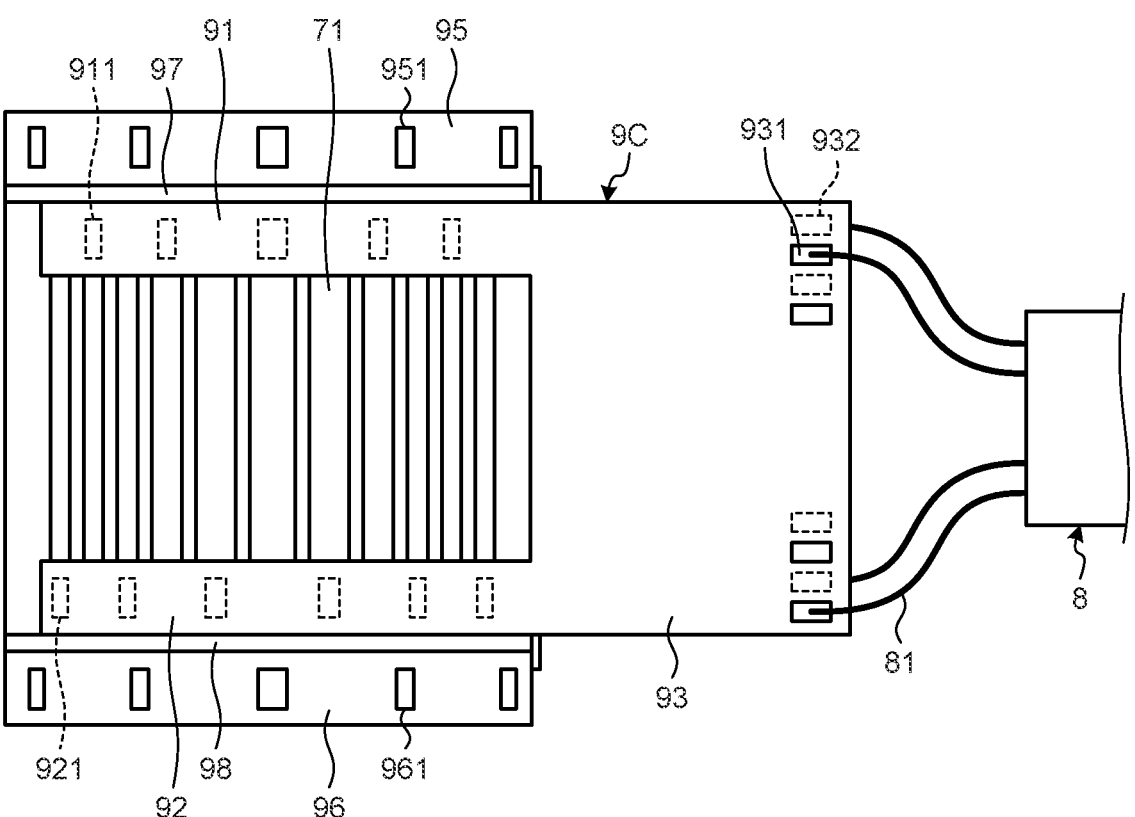
FIG. 13 is a diagram (Part 1) illustrating a configuration of an essential part of the ultrasound transducer array included in the ultrasound endoscope according to a third embodiment of the disclosure.

Next, a third embodiment of the disclosure will be explained, referring to FIG. 13. FIG. 13 is a diagram illustrating a configuration of an essential part of an ultrasound transducer array included in an ultrasound endoscope according to the third embodiment of the disclosure. The endoscope system according to the third embodiment has a configuration similar to the endoscope system 1 described above except a change in the relay board. The third embodiment includes a relay board 9C instead of the relay board 9 of the first embodiment described above. In the following, a configuration different from the first embodiment described above (relay board 9C) will be explained.

The relay board 9C is branched at an end portion on one end side of the relay board 9C, and is connected to the transducer 71 on the branched side and is connected to the internal ultrasonic-signal cable 8 at an end portion on another end side of the relay board 9C. The relay board 9C includes the first extension portion 91, the second extension portion 92, the connection portion 93, a first test piece 95, a second test piece 96, a first joint portion 97, and a second joint portion 98. The relay board 9C is constituted of a bendable FPC similarly to the relay board 9 described above.

The first test piece 95 extends in parallel with the first extension portion 91, and is electrically connected to a test device. In the first test piece 95, plural electrode portions 951 (fourth electrode portion) to be connected to the test device are formed. The respective electrode portions 951 are electrically connected to the corresponding electrode portions 911 in the first extension portion 91 through the first joint portion 97.

The second test piece 96 extends in parallel with the second extension portion 92, and is electrically connected to a test device. In the second test piece 96, plural electrode portions 961 (fifth electrode portion) to be connected to the test device are formed. The respective electrode portions 961 are electrically connected to the corresponding electrode portions 921 in the second extension portion 92 through the second joint portion 98.

The first joint portion 97 extends in parallel with the first extension portion 91, and joins the first extension portion 91 and the first test piece 95.

The second joint portion 98 extends in parallel with the second extension portion 92, and joins the second extension portion 92 and the second test piece 96.

When a continuity test and the like of the transducer 71 is performed by using the test device, the test device and the electrode portions 951 and 961 are connected to each other. After the test is finished, by cutting off the first joint portion 97 and the second joint portion 98 by using, for example, a dicing saw, it becomes the same configuration as the relay board 9. Assembly processing of the ultrasound transducer array after the first joint portion 97 and the second joint portion 98 are cut off is the same as the first embodiment.

In the third embodiment explained above, the relay board 9C in which the first test piece 95 is joined to the first extension portion 91 through the first joint portion 97, and the second test piece 96 is joined to the second extension portion 92 through the second joint portion 98 is constructed. In the relay board 9C, the electrode portions 951 and 961 connected to the test device are arranged, and an operation test of the transducer 71 can be performed by the electrode portions 931 and 932 of the connection portion 93 from different positions. After the test, by cutting off the first joint portion 97 and the second joint portion 98, the ultrasound transducer array can be obtained. By increasing the size of the first test piece 95 and the second test piece 96, a pitch of respective electrode portions of the electrode portions 951 and 961 can be increased, and the continuity test is facilitated to be performed.

In the third embodiment, to smoothly perform cut off of the first joint portion 97 and the second joint portion 98, an indicator indicating a cut-off position may be provided. The indicator includes, for example, a cutting line, a perforation intermittently perforated, and the like.

Fourth Embodiment

Figure 14:
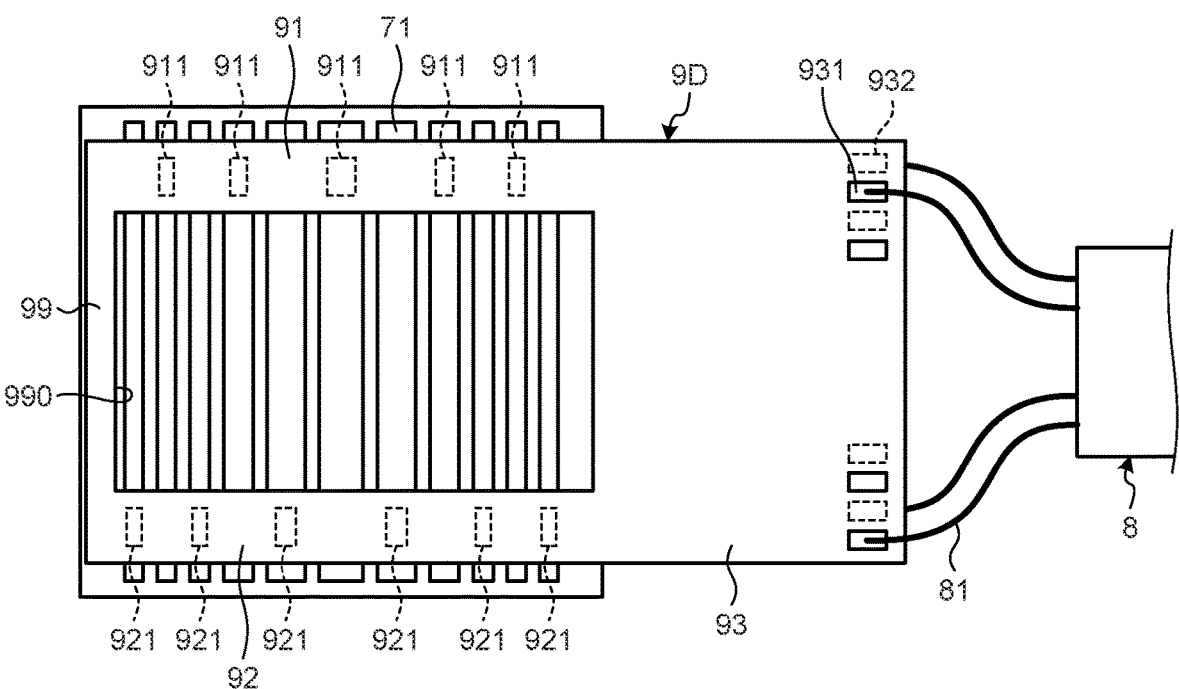
FIG. 14 is a diagram illustrating a configuration of an essential part of an ultrasound transducer array included in an ultrasound endoscope according to a fourth embodiment of the disclosure.

Next, a fourth embodiment of the disclosure will be explained, referring to FIG. 14. FIG. 14 is a diagram illustrating a configuration of an essential part of an ultrasound transducer array included in an ultrasound endoscope according to a fourth embodiment of the disclosure. An endoscope system according to the fourth embodiment has a configuration similar to the endoscope system 1 described above except a change in the relay board. The fourth embodiment includes a relay board 9D instead of the relay board 9 of the first embodiment described above. In the following, a configuration different from the first embodiment described above (relay board 9D) will be explained.

The relay board 9D is branched at an end portion on one end side of the relay board 9D, and is connected to the transducer 71 on the branched side and is connected to the internal ultrasonic-signal cable 8 at an end portion on another end side of the relay board 9D. The relay board 9D includes the first extension portion 91, the second extension portion 92, the connection portion 93, and a bridge portion 99. The relay board 9D is constituted of a bendable FPC similarly to the relay board 9 described above. The configuration of the first extension portion 91, the second extension portion 92, and the connection portion 93 is same as that of the first embodiment.

The bridge portion 99 has one end that is connected to an end portion of the first extension portion 91 on the opposite side to the connection portion 93, and another end that is connected to an end portion of the second extension portion 92 on the opposite side to the connection portion 93.

In the relay board 9D, with the first extension portion 91, the second extension portion 92, the connection portion 93, and the bridge portion 99, an opening portion 990 that pierces through in a direction of board thickness of the relay board 9D, and that forms closed space is arranged. The relay board 9D is electrically connected to the transducer 71 at portions extending along the direction of alignment of the transducers 71 (the first extension portion 91 and the second extension portion 92 in this example) in periphery of the opening portion 990.

Moreover, assembly of the ultrasound transducer array is the same as the first embodiment.

In the fourth embodiment explained above, similarly to the first embodiment, the relay board 9D that relays signal transmission between the transducer 71 and the signal line 81 has a bifurcated structure at an end portion of the relay board 9D on a side connected to the transducers 71, and the electrode portions 911 and 921 formed in the first extension portion 91 and the second extension portion 92 are connected to the respective transducers 71. By splitting connection to the transducers 71 into two, a distance between electrodes can be increased, and an effect similar to that of the first embodiment can be obtained.

Furthermore, according to the fourth embodiment, the relay board 9D has a ring shape on a side connected to the transducer portion 7, and with the bridge portion 99, the end portion of the first extension portion 91 on the side of the bridge portion 99 and an end portion of the second extension portion 92 on the side of the bridge portion 99 can be connected to the transducer portion 7 without being separated from each other, while maintaining a certain distance between the first extension portion 91 and the second extension portion 92. As a result, it is possible to stabilize the connection position of the relay board 9D with respect to the transducer portion 7.

Fifth Embodiment

Figure 15:
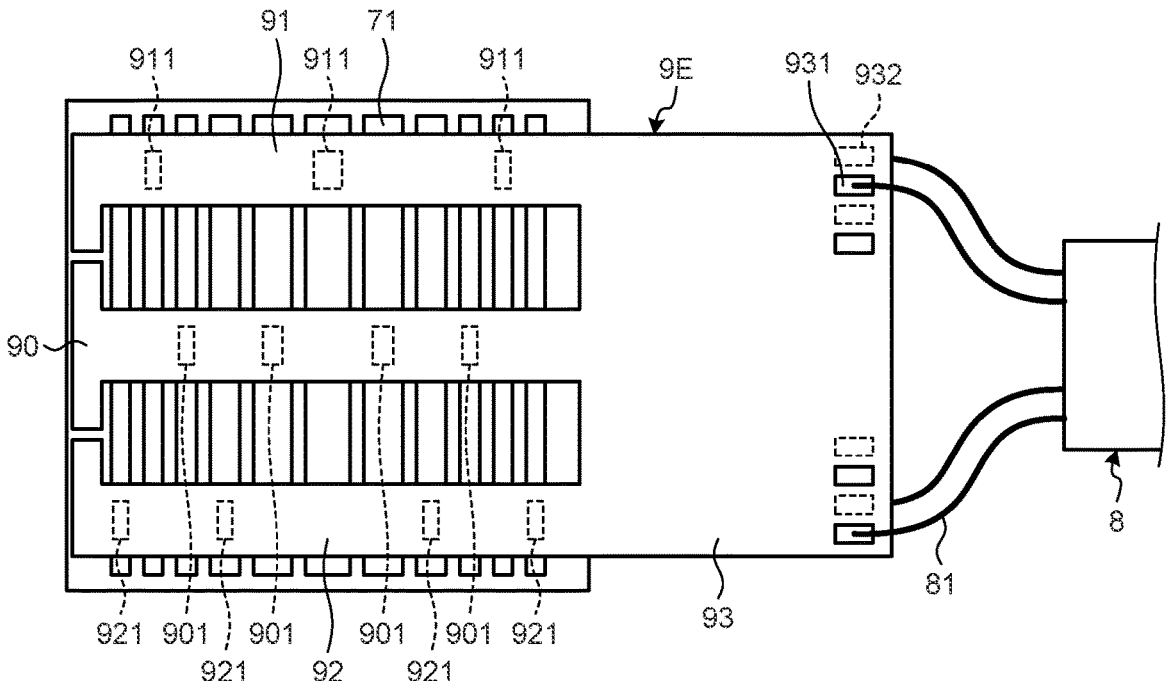
FIG. 15 is a diagram illustrating a configuration of an essential part of an ultrasound transducer array included in an ultrasound endoscope according to a fifth embodiment of the disclosure.

Next, a fifth embodiment of the disclosure will be explained, referring to FIG. 15. FIG. 15 is a diagram illustrating a configuration of an essential portion of an ultrasound transducer array included in an ultrasound endoscope according to the fifth embodiment of the disclosure. An endoscope system according to the fifth embodiment has a configuration similar to the endoscope system 1 described above except a change in the relay board. The fifth embodiment includes a relay board 9E instead of the relay board 9 of the first embodiment described above. In the following, a configuration different from the first embodiment described above (relay board 9E) will be explained.

The relay board 9E is branched at an end portion on one end side of the relay board 9E, and is connected to the transducer 71 on the branched side and is connected to the internal ultrasonic-signal cable 8 at an end portion on another end side of the relay board 9E. The relay board 9E includes the first extension portion 91, the second extension portion 92, the connection portion 93, and a third extension portion 90. The relay board 9E is constituted of a bendable FPC similarly to the relay board 9 described above.

The third extension portion 90 is arranged on one end side of the longitudinal direction of the transducer 71, extends in the direction of alignment of the transducers 71, and is connected to some of the transducers 71. Moreover, the third extension portion 90 is connected to an end portion of the connection portion 93 on the opposite side to the side on which the electrode portions 931 and 932 are formed. In the third extension portion 90, plural electrode portions 901 that are respectively connected to the transducers 71 are formed.

The first extension portion 91, the second extension portion 92, and the third extension portion 90 are connected to the different transducers 71 from one another. In the second extension portion 92, the plural electrode portions 921 that are respectively connected to the transducers 71 are formed. The respective electrode portions 911, 921, and 901 are connected to the different transducers 71 from one another. At this point, the electrode portions formed in each of the same extension portion are not connected to transducers adjacent to each other in the direction of alignment, but connected to the transducers 71 maintaining an interval of at least one.

Moreover, assembly of the ultrasound transducer array is the same as the first embodiment except that the electrode portion 901 of the third extension portion 90 and the transducer 71 are connected.

In the fifth embodiment explained above, similarly to the first embodiment, the relay board 9E that relays signal transmission between the transducer 71 and the signal line 81 has a trifurcated structure at an end portion of the relay board 9E on a side connected to the transducers 71, and the electrode portions 911, 921, and 901 formed in the first extension portion 91, the second extension portion 92, and the third extension portion 90 are connected to the respective transducers 71. By splitting connection to the transducers 71 into multiple ways, a distance between electrodes can be increased, and an effect similar to that of the first embodiment can be obtained.

In the fifth embodiment, FIG. 15 shows an example of a shape in which the respective extension portions have a larger width at the end portion on the opposite side to the connection portion 93 side than another portion of the respective extension portions, but it is not limited thereto. For example, the respective extension portions may extend with a uniform width, or some of the extension portions may have a shape extending with a different width from the other extension portions. The width herein is a length in a direction perpendicular to both of an extending direction of the extension portion and the direction of board thickness of the extension portion.

Sixth Embodiment

Figure 16:
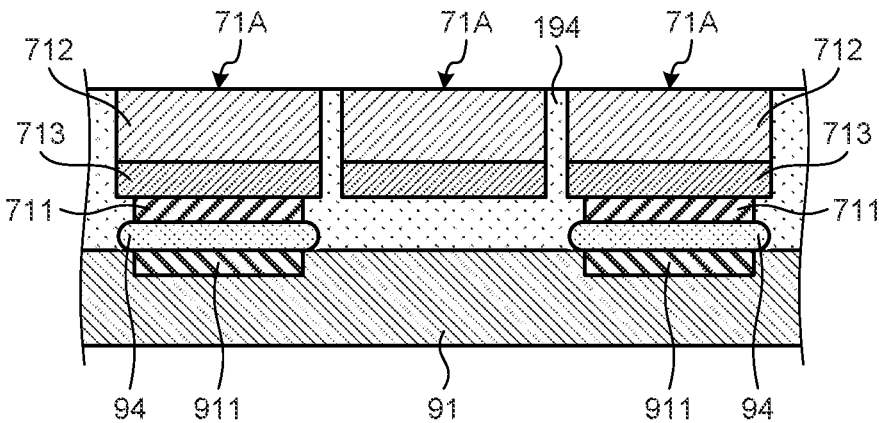
FIG. 16 is a diagram illustrating a configuration of an essential part of an ultrasound transducer array included in an ultrasound endoscope according to a sixth embodiment of the disclosure.

Next, a sixth embodiment of the disclosure will be explained, referring to FIG. 16. FIG. 16 is a diagram illustrating a configuration of an essential part of an ultrasound transducer array included in an ultrasound endoscope according to the sixth embodiment of the disclosure. FIG. 16 is a cross-section illustrating a connection portion between a transducer 71A and the first extension portion 91, and is a cross-section cut along a plane perpendicular to a longitudinal direction of the transducer 71A. The endoscope system according to the sixth embodiment has a configuration similar to the endoscope system 1 described above except a change in the transducer. In the sixth embodiment, instead of the transducer 71 of the first embodiment described above, a transducer 71A is provided. In the following, a configuration different from the first embodiment described above (transducer 71A) will be explained.

Each of the transducers 71A has a prism shape, and the transducers 71A are arranged such that longitudinal directions of the transducers 71A are aligned. The transducer 71A is constituted of a device portion 712 and a dematching layer 713 laminated. The dematching layer 713 may be configured to serve a role as an electrode itself.

The device portion 712 transmits and receives ultrasonic waves.

The dematching layer 713 reflects an ultrasonic wave that propagates on the dematching layer 713 side, which is the opposite side to the acoustic matching layer 73, in ultrasonic waves emitted by the device portion 712 to the device portion 712 side. By the reflection of the dematching layer 713, an ultrasonic wave that travels to the opposite side to the subject from the device portion 712 is transmitted to the subject side.

According to the sixth embodiment, an effect similar to that of the first embodiment described above can be obtained, and it is possible to further ensure that an ultrasonic wave emitted from the transducer 71A is transmitted to the subject.

The embodiments to implement the disclosure have so far been explained, but the disclosure is not to be limited only to the embodiments described above. The disclosure can include various embodiments not describe herein and the like. For example, an example in which an internal ultrasonic-signal cable is connected to both sides of a relay board has been explained in the embodiment described above, but it may be connected only on one side.

The ultrasound transducer array and the manufacturing method of the endoscope and the ultrasound transducer array according to the disclosure are useful for suppressing deterioration in quality of an ultrasound device.

According to the disclosure, an effect that a possibility of quality deterioration of an ultrasound device can be suppressed is produced.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound transducer array comprising:
   a transducer group including a plurality of ultrasound transducers aligned, the transducers being configured to transmit and receive ultrasonic waves;
   a signal line configured to electrically connect the transducer group and an external device and transmit a signal communicated by the transducer group and the external device; and
   a relay board that is a bendable relay board and that has a first end and a second end, the first end being branched, the first end being connected to each of the ultrasound transducers, the second end being connected to the signal line to relay transmission and reception of the signal between the ultrasound transducers and the signal line, branched portions of the first end of the relay board extending in a direction of alignment of the ultrasound transducers.

2. The ultrasound transducer array according to claim 1, wherein
   the relay board has a structure in which the first end is branched into two,
   the relay board includes
      a first extension portion that is connected to some of the ultrasound transducers;
      a second extension portion that is connected to remaining ultrasound transducers of the ultrasound transducers; and
      a connection portion that is connected to the signal line, and joined with the first extension portion and the second extension portion on an opposite side to a side connected to the signal line.

3. The ultrasound transducer array according to claim 2, wherein each of the ultrasound transducers extends in a pillar shape, electrodes are alternately provided at a first end or a second end of a longitudinal direction of each of the ultrasound transducers in the direction of alignment of the ultrasound transducers, and in the relay board, the first extension portion and the second extension portion are connected to the ultrasound transducers alternately in the direction of alignment of the ultrasound transducers.

4. The ultrasound transducer array according to claim 3, wherein the first extension portion and the second extension portion have a plurality of electrode portions connected to the ultrasound transducers, and each of the electrode portions has a flying lead structure.

5. The ultrasound transducer array according to claim 2, wherein each of the ultrasound transducer extends in a pillar shape, electrodes are alternately provided at a first end or a second end of a longitudinal direction of each of the ultrasound transducers in the direction of alignment of the ultrasound transducers, the relay board further includes a third extension portion that extends in a direction of extension of the first extension portion, and that includes a second electrode portion;

a fourth extension portion that extends in a direction of extension of the second extension portion, and that includes a third electrode portion;

a first joint portion configured to join the first extension portion and the third extension portion; and a second joint portion configured to join the second extension portion and the fourth extension portion.

6. The ultrasound transducer array according to claim 1, wherein in the ultrasound transducer group, the ultrasound transducers are aligned in a curved manner in an arch, and the branched portions of the relay board are curved in an arch following the direction of alignment of the ultrasound transducers, and are connected to an inner periphery of an arc formed by the transducer group.

7. The ultrasound transducer array according to claim 1, wherein the ultrasound transducers and the relay board are bonded by electrically conductive adhesive.

8. An endoscope comprising:

an insertion portion configured to be inserted to an inside of a subject; and an ultrasound transducer array that includes a transducer group that is arranged at a distal end of the insertion portion and that includes a plurality of ultrasound transducers aligned, the transducers being configured to transmit and receive ultrasonic waves;

a signal line configured to electrically connect the transducer group and an external device and transmit a signal communicated by the transducer group and the external device; and a relay board that is a bendable relay board and that has a first end and a second end, the first one end being branched, the first end being connected to each of the ultrasound transducers, the second end being connected to the signal line to relay transmission and reception of the signal between the ultrasound transducers and the signal line, branched portions of the first end of the relay board extending in a direction of alignment of the ultrasound transducers.

9. An ultrasound transducer array comprising:

a transducer group including a plurality of ultrasound transducers aligned, the transducers being configured to transmit and receive ultrasonic waves;

a signal line configured to electrically connect the transducer group and an external device and transmit a signal communicated by the transducer group and the external device; and a relay board having a first end and a second end, the first end being connected to each of the ultrasound transducers, the second end being connected to the signal line to relay transmission and reception of the signal between the ultrasound transducers and the signal line, the relay board including an opening portion configured to expose a part of the ultrasound transducers, the relay board being electrically connected to the ultrasound transducers at a portion extending in a direction of alignment of the ultrasound transducers in peripheral portions of the opening portion.

\* \* \* \* \*